United States Patent [19]

Kurth

[11] Patent Number: 5,069,229

[45] Date of Patent: Dec. 3, 1991

[54] METHOD AND APPARATUS FOR THE REDUCTION OF SOFT TISSUE INJURY IN A FEMORALLY CATHETERIZED PATIENT

[76] Inventor: Paul A. Kurth, 1423 Brett Pl., San Pedro, Calif. 90732

[21] Appl. No.: 468,199

[22] Filed: Jan. 22, 1990

[51] Int. Cl.⁵ .............................................. A61F 5/37
[52] U.S. Cl. ..................................... 128/877; 128/882
[58] Field of Search ............... 128/877, 878, 879, 882, 128/80 F, 80 C, DIG. 6, 80 R, 80 G, 87 R, DIG. 26, 80 F; 604/181, 49–53; 5/431, 437

[56] References Cited

U.S. PATENT DOCUMENTS

| | | | |
|---|---|---|---|
| 1,696,763 | 12/1928 | Hare | 128/DIG. 26 |
| 3,480,013 | 11/1969 | Garber | 128/873 |
| 3,590,817 | 7/1971 | Wresch | 128/877 |
| 3,903,878 | 9/1975 | Spann | 128/80 R |
| 3,939,829 | 2/1976 | Spann | 128/80 R |
| 4,372,299 | 2/1983 | Fixel | 128/882 |
| 4,393,866 | 7/1983 | Finnieston | 128/87 R |
| 4,438,763 | 3/1984 | Zablen | 128/DIG. 6 |
| 4,470,410 | 9/1984 | Elliott | 128/DIG. 26 |
| 4,520,805 | 6/1985 | St. Vincent | 128/80 R |
| 4,671,787 | 6/1987 | Widman | 128/DIG. 26 |
| 4,690,674 | 9/1987 | Dalglish | 128/DIG. 6 |
| 4,690,675 | 9/1987 | Katz | 128/DIG. 26 |
| 4,886,258 | 12/1989 | Scott | 128/87 R |

Primary Examiner—Robert A. Hafer
Assistant Examiner—Michael Brown
Attorney, Agent, or Firm—Daniel L. Dawes

[57] ABSTRACT

Soft tissue injury in a recuperating patient who has an implanted object or guide tube in a femoral incision is avoided or substantially reduced by preventing or reducing hip flexure. Hip flexure is avoided or reduced by immobilizing the knee of the leg in which the femoral incision has been made. The knee is immobilized by a device which prevents flexure of the knee. The knee is further immobilized by positionally fixing the knee, thereby preventing medial, anterior and posterior movements. An orthopedic knee immobilizer is utilized to prevent knee flexure. The orthopedic knee immobilizer is connected to a strap which in turn is fixed to the bed or surface upon which the recuperating patient lies. In this manner, unconscious or involuntary movements made during sleep which might otherwise cause severe hematomas in the groin or near the femoral incision are substantially avoided.

6 Claims, 1 Drawing Sheet

METHOD AND APPARATUS FOR THE REDUCTION OF SOFT TISSUE INJURY IN A FEMORALLY CATHETERIZED PATIENT

BACKGROUND OF THE INVENTION

1. Field of the Invention

The invention is in the field of medical equipment and more specifically relates to an apparatus for preventing flexure of a patient's hip in order to avoid soft tissue injury in a patient's leg who has femorally catheterized.

2. Description of the Prior Art

It is necessary in many types of cardiovascular operations or treatments, particularly those involving an endovascular technique, to access the cardiovascular system of a patient through a femoral artery. An incision is made in the leg below and adjacent the groin into the femoral artery. A guiding catheter is inserted into the incision through which an endovascular catheter or other device is disposed for the purposes of the surgical treatment or medical procedure. For example, angioplastic surgery is routinely performed through a femoral incision. A relatively rigid tube is thus placed within the incision and left in place for purposes of guiding the endovascular catheter and to avoid abrasion or further injury or damage to the soft tissues while the endovascular catheter is manipulated.

After the procedure is completed, the guide tube is often left in place and then coupled to an intravenous feed device through which fluids, antibiotics, anticoagulants or other drugs can be continuously or periodically administered during the first hours or days after the endovascular procedure is completed.

Typically, after angioplastic surgery the patient is confined to a bed and provided with intravenous feeding as described above at least through an overnight period. The guide tube is secured in place with tape or bandaging in order to prevent its movement or dislodgment during the initial recuperation period. Very often the patient is sore or tender from the operation and is little inclined in any case to make large or forceful movements while confined to the bed. Additionally the patient's cooperation is requested to voluntarily refrain from making any movements which would disturb the guide tube or aggravate the injury inherent with the femoral incision.

However, even the most disciplined and most cooperative patient will invariably make repeated hip or leg movements while confined in the bed while asleep or unconscious. The result is that many patients will wake the following morning and find that they have a large hematoma in the groin region or in the area of the femoral incision. This hematoma is caused by involuntary sleep movements resulting in soft tissue injury and internal bleeding as the guide tube inserted into the femoral incision is abused by such sleep movements.

The prior art has not devised any means for preventing or reducing such soft tissue injury in femorally catheterized patients other than attempting to fix the guide tube relative to the thigh by taping and bandaging. As stated above, such prior art attempts are often ineffective and in some cases even dramatically ineffective. While the prior art has devised various means in connection with orthopedic surgery for preventing or controlling movement of a patient's hips or limbs for the purposes of treating bone injury diseases, no such teaching is known with respect to prevention of soft tissue injury. See, for example, St. Vincent et al., "Abductor Turntable", U.S. Pat. No. 4,520,805 (1985), for immobilizing the ball and socket joint of a patient's hip and numerous patient restraint devices, typically used with violent, uncontrollable patients or prisoners such as shown by Condit, "Restraining Device", U.S. Pat. No. 2,215,454 (1940) and Brill, "Restraining Device", U.S. Pat. No. 2,679,842 (1954).

Therefore, what is needed is an apparatus and method whereby soft tissue injury to a femorally catheterized patient can be prevented or at least substantially reduced even from unconscious sleep movements.

BRIEF SUMMARY OF THE INVENTION

The invention is a method for reducing soft tissue injury associated with implantation of an object in a femoral incision comprising the steps of implanting the object in the femoral incision, and reducing hip movement of at least that portion of the hip adjacent to the femoral incision by immobilizing the knee to prevent flexure of the knee.

As a result, soft tissue injury related to the implanted object within the femoral incision is substantially avoided.

The step of immobilizing the knee comprises disposing the knee within a restraint. The knee is disposed in one embodiment in a split tapered wrapping fixed around, above and below the knee. The wrapping has a predetermined stiffness tending to prevent flexion of the knee. The step of immobilizing the knee comprises the step of generally fixing the knee near or to a predetermined fixed location.

The step of strapping the knee down comprises the step of affixing a strap to the restraint, and selectively fixing the strap to position the restraint near the predetermined position.

Where the patient recuperates on a bed structure, the step of fixing the strap comprises the step of fixing the strap to the bed structure.

The invention can also be characterized as a method for reducing soft tissue injury to a recuperating patient having an implanted object in a femoral incision comprising the steps of providing a knee restraint for preventing flexure of the knee, and fitting the knee restraint to the knee of the leg wherein the femoral incision has been made.

As a result, unconscious or sleep movements of the hip of the patient are substantially reduced and soft tissue injury related to implantation of the object in the femoral incision are substantially avoided.

The method further comprises the step of providing a second knee restraint and fitting the second knee restraint above, about and below the knee of the leg of the patient opposite to the leg wherein the femoral incision has been made.

The invention is still further characterized as an apparatus for reducing soft tissue injury to a recuperating patient from an implanted object in a femoral incision comprising a device for immobilizing the knee of the patient of the leg wherein the femoral incision has been made, and a device for fixing the position of the immobilized knee.

As a result, unconscious or involuntary hip movements made while asleep are substantially reduced and soft tissue injury to the femoral incision from the implanted object correspondingly reduced.

The device for immobilizing the knee may be an orthopedic knee immobilizing device.

The apparatus further comprises a mechanism for providing attachment to a medical device temporarily locally positioned relative to the femoral incision for treatment of the patient.

The invention can better be visualized by turning to the following drawings where like numerals reference like elements.

The invention and its various embodiments may now be better understood by turning to the following detailed description.

DETAILED DESCRIPTION OF THE PREFERRED EMBODIMENTS

Soft tissue injury in a recuperating patient who has an implanted object or guide tube in a femoral incision is avoided or substantially reduced by preventing or reducing hip flexure. Hip flexure is avoided or reduced by immobilizing the knee of the leg in which the femoral incision has been made. The knee is immobilized by a device which prevents flexure of the knee. The knee is further immobilized by positionally fixing the knee, thereby preventing medial, anterior and posterior movements. An orthopedic knee immobilizer is utilized to prevent knee flexure. The orthopedic knee immobilizer is connected to a strap which in turn is fixed to the bed or surface upon which the recuperating patient lies. In this manner, unconscious or involuntary movements made during sleep which might otherwise cause severe hematomas in the groin or near the femoral incision are substantially avoided.

Figure 1:
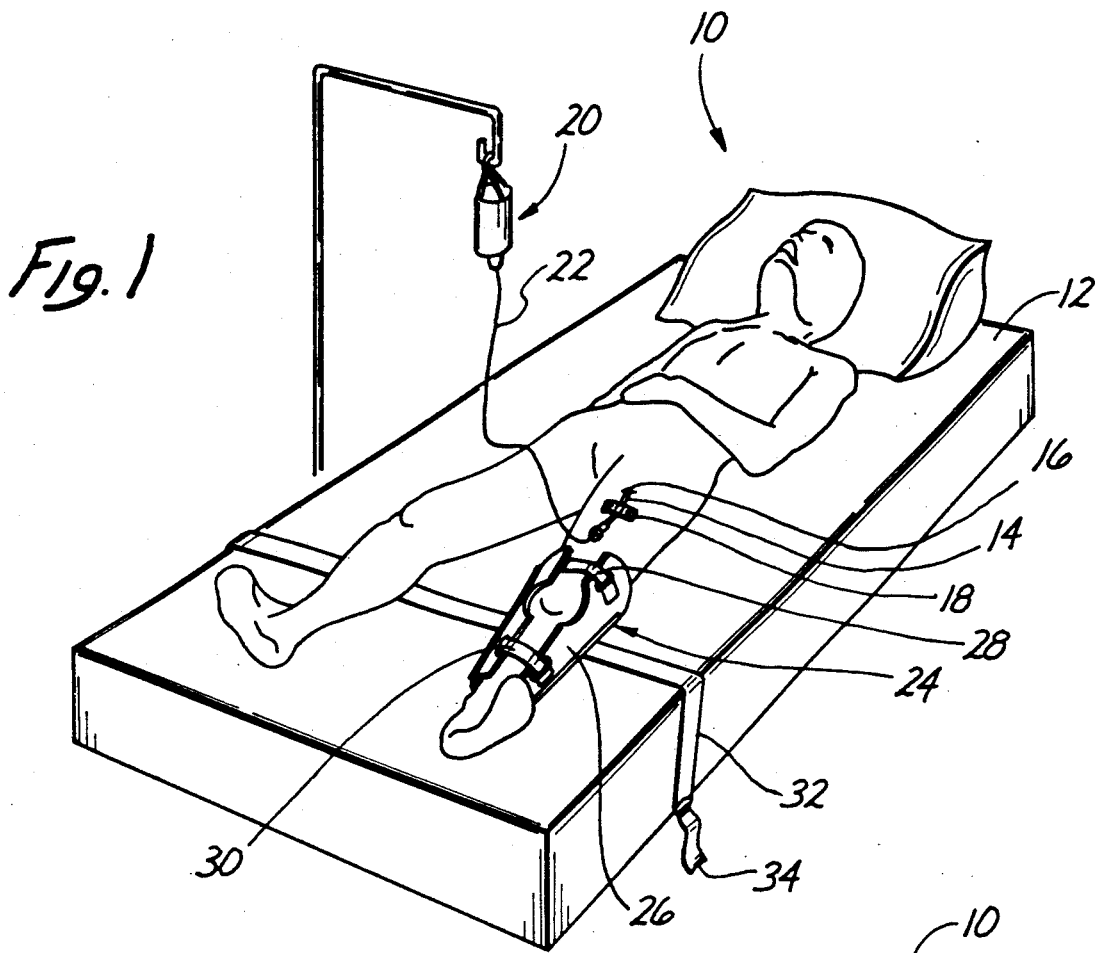
FIG. 1 is an idealized perspective view of a patient fitted with an apparatus according to the invention so as to prevent soft tissue injury.

FIG. 1 illustrates in diagrammatic perspective view a patient 10 lying prone upon a conventional hospital bed 12. The patient shown in FIG. 1 has undergone an endovascular procedure involving a femoral incision which has been completed. While the patient recuperates, a guide tube 14, possibly used during the endovascular procedure, remains implanted within the femoral incision 16.

As illustrated in FIG. 1, guide tube 14 is secured in place relative to the patient's thigh by means of tape or bandaging 18 in a manner conventional in the art. Guide tube 14 in the illustration of FIG. 1 is coupled to an intravenous feed device generally denoted by reference numeral 20. Feed device 20 is coupled to guide tube 14 through tubing 22. Fluids, antibiotics, anticoagulants or other drugs may be provided through intravenous feed device 20 through tubing 22 and guide tube 14 to patient 10 during all or a substantial portion of the recuperation period, which may extend from several hours to several days.

Thus, patient 10 may be confined and guide tube 14 will remain implanted within the femoral incision 16 for at least one overnight or sleeping/unconscious period of patient 10.

Figure 2:
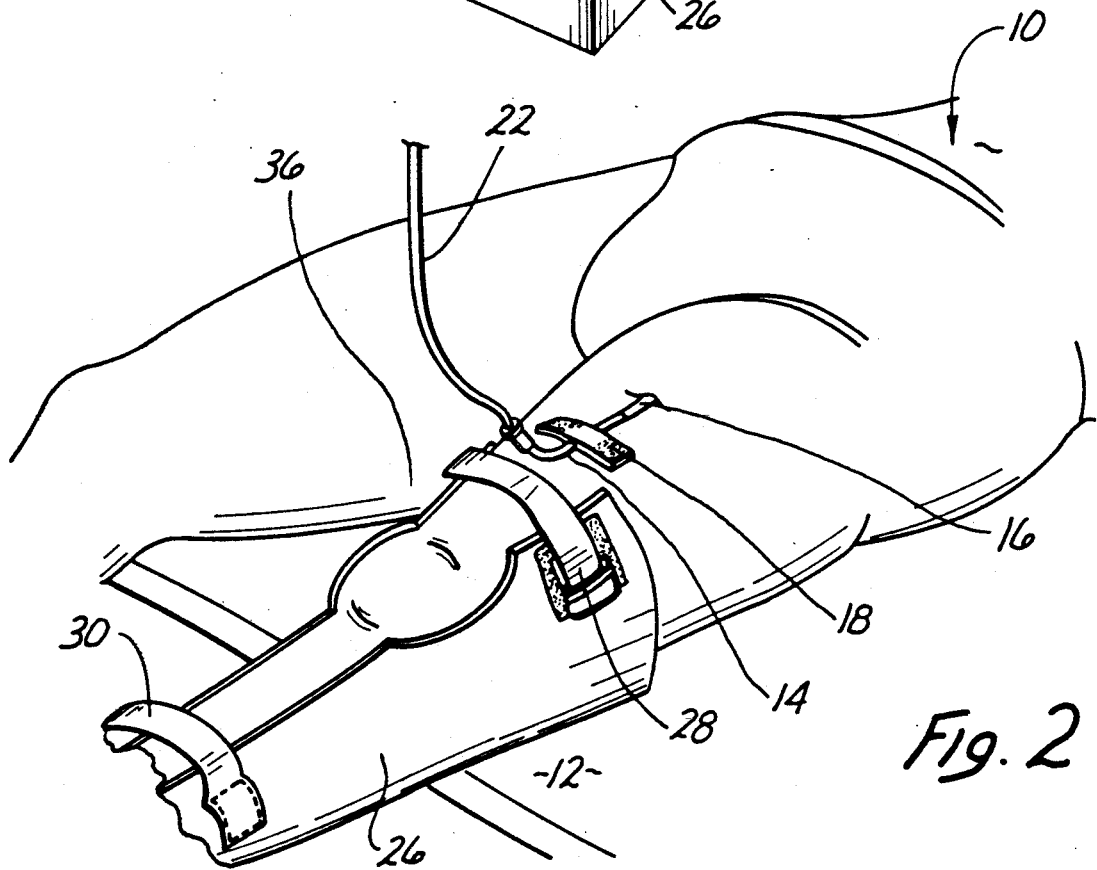
FIG. 2 is an enlarged perspective view of the upper leg and groin region of the patient shown in FIG. 1 and illustrating in greater detail the methodology and apparatus of the invention.

It has been discovered by the applicant that much of the soft tissue injury which occurs to a convalescing patient with an implanted guide tube 14 occurs due to hip movements, typically made while unconscious or asleep. It has further been determined by the applicant that such involuntary hip movements can be substantially reduced or prevented by immobilizing one or both knees of the patient, preferably at least that knee of the leg in which femoral incision 16 has been made as depicted in FIGS. 1 and 2.

The probability or ability of the patient to flex at the hip or groin and thereby cause soft tissue injury to occur at or near femoral incision 16 is substantially lessened if the entire weight of the leg must be lifted or moved in order to cause the hip flexure. Therefore, a means 24 for immobilizing the knee is shown in FIGS. 1 and 2. In the illustrated embodiment the immobilization means 24 is comprised of a split tapered cylindrical foam shell 26 which can be wrapped about the knee and extend both above and below the knee. Shell 26 is split along its longitudinal length in a direction parallel to the leg and extends as an integral continuous body or sheet around an beneath the leg and knee. Shell 26 of immobilization means 24 is snugly fastened about the leg by an upper strap 28 and lower strap 30 best illustrated in FIG. 2. Straps 28 and 30 are formed at the upper and lower edge respectively of the tapered split cylindrical form comprised of sheet 26, and in the illustrated embodiment includes a conventional Velcro fastener. Additional shaped layers of split tapered foam (not shown) may be included within outer sheet 26, which is exposed and shown in FIGS. 1 and 2, to provide more rigidity to immobilization means 24 and to provide a closer and more snug fit with the sides and back of the leg, knee and calf. Immobilization means 24, to the extent thus far described, may in fact be similar to conventional knee immobilizers used in orthopedic surgery.

The particular form of device or means by which flexure at the knee is prohibited is largely immaterial to the invention. Thus, any means now known or later described which may be utilized to prevent knee flexure may be utilized with full equivalency.

However, although knee immobilization tends to reduce the probability that the patient will even unconsciously flex at the hip or groin, it is further contemplated within the invention that immobilization means 24 shall include a means for fixing the location or position of the patient's knee or leg.

In the illustrated embodiment immobilization means 24 is fixed at a predetermined position on bed 12 by means of a strap 32 which is fixed or connected to the rear of sheet 26 in a manner not shown. In the illustrated manner the fixation of strap 32 to the back of sheet 26 is by means of stitching but other means including buckles, clasps, snaps or the like may be equivalently employed.

Strap 32 is a strong flat fabric strap which is long enough to be laid transversely across bed 12 underneath patient 10. The ends 34 of strap 32, one of which is shown in FIG. 1, are sufficiently long to tie or provide attachment to a lower portion of bed 12. Again, the particular means by which strap 32 is affixed to bed 12 is largely immaterial to the invention, as along as strap 32, within the limits of its rigidity and elasticity, tends to retain knee immobilization means 24 at or near a predetermined fixed location on bed 12.

In the illustrated embodiment, end 34 of strap 32 is simply tied around a lower portion of the bed frame. However, strap 32 could as well be coupled to the bed or bedding through Velcro fasteners, buckles, snaps, clamps or other equivalent means.

Therefore, not only is the patient's knee prevented from making any large flexures, the position of the knee is maintained so that any large conscious or unconscious medial movements transversely across the bed, any longitudinal movements toward the head or foot of the bed by the patient's leg or body, or any vertical movements in or out of the plane of the bed surface is prevented or at least substantially reduced.

The result is that although the patient's body or hip is not otherwise bound or restricted, and the patient is left to lie comfortably and largely unrestrained within the bed, but hip flexures are substantially prevented or reduced so that soft tissue injury which may unintentionally or unconsciously otherwise result is avoided. The relatively hard guide tube 14 may thus remain in place for substantial periods of time, especially during unconscious or sleeping periods, without the danger or almost inevitable result of a hematoma or other soft tissue injury occurring.

Furthermore, immobilization means 24 provides an additional platform for an affixation site for other medical devices in the proximity of femoral incision 16. In many cases a drug injection device 36 can be clipped, clamped, snapped, tied, buttoned or otherwise permanently or temporarily attached to any part of knee immobilization means 24, such as sheet 26 or straps 28 or 30, and be connected or coupled with tubing 22 or guide tube 14. The prior art practice with such devices has been to temporarily suture device 36 to the patient's leg. Although such suturing can be expected to cause minor injury to the person's leg relative to the femoral incision 16, the apparatus and methodology of the present invention completely obviates the need for even risking minor injury through unnecessary suturing by providing a proximate and convenient attachment surface for such devices and procedures.

Many modifications and alterations may be made by those having ordinary skill in the art without departing from the spirit and scope of the invention. Therefore, the illustrated embodiment must be understood as being set forth only for purposes of example and not as limiting the invention as defined in the following claims which are to be construed as including not only the means depicted in the above description and drawings, but all mechanisms which can perform the same function, albeit in a different way.

I claim:

1. A method for reducing soft tissue injury associated with implantation of an object in a femoral incision in a leg comprising the steps of:
   implanting said object in said femoral incision; and
   reducing hip movement of at least that portion of the hip adjacent to said femoral incision by immobilizing only the knee portion corresponding to said leg to prevent flexure of said knee,
   whereby soft tissue injury related to said implanted object within said femoral incision is substantially avoided.

2. The method of claim 1 where said step of immobilizing said knee comprises the step of generally fixing said knee near a predetermined fixed location to prevent medial, vertical and longitudinal movement of said knee.

3. The method of claim 2 wherein said step of generally fixing said knee comprises the step of strapping said knee down to a predetermined point.

4. A method for reducing soft tissue injury to a recuperating patient having an implanted object in a femoral incision comprising the steps of:
   providing a knee restraint for preventing flexure of said knee; and
   fitting said knee restraint only to said knee of the leg wherein said femoral incision has been made,
   leaving the other leg free and leaving other portions of said corresponding leg free,
   whereby unconscious or sleep movements of the hip of the patient are substantially reduced and soft tissue injury related to implantation of said object in said femoral incision are substantially avoided.

5. The method claim 4 further comprising the step of fixing the position of said knee restraint.

6. The method of claim 4 further comprising the step of providing a second knee restraint and fitting said second knee restraint above, about and below the knee of the leg of said patient opposite to the leg wherein said femoral incision has been made.

* * * * *